United States Patent [19]

Liu et al.

[11] Patent Number: 5,322,601
[45] Date of Patent: Jun. 21, 1994

[54] AMPEROMETRIC GAS SENSOR TO SELECTIVELY DETERMINE THE PARTIAL PRESSURES OF A GAS

[75] Inventors: Jun Liu; Werner Weppner, both of Stuttgart, Fed. Rep. of Germany

[73] Assignee: Max-Planck-Gesellschaft zur Forderung der Wissenschaften e.V., Gottingen, Fed. Rep. of Germany

[21] Appl. No.: 868,145

[22] Filed: Apr. 14, 1992

[30] Foreign Application Priority Data

Apr. 15, 1991 [DE] Fed. Rep. of Germany ....... 4112302

[51] Int. Cl.$^5$ ............................................. G01N 27/26
[52] U.S. Cl. .......................... 204/153.18; 204/153.15
[58] Field of Search ..................... 204/153.18, 153.15, 204/424, 425, 426

[56] References Cited

U.S. PATENT DOCUMENTS 4,855,034  8/1989  Sugimoto et al. .............. 204/153.18
4,875,981 10/1989  Usami et al. .................... 204/153.18

Primary Examiner—John Niebling
Assistant Examiner—Bruce F. Bell
Attorney, Agent, or Firm—Nikaido, Marmelstein Murray & Oram

[57] ABSTRACT

The invention concerns as amperometric gas sensor for the selective determination with high accuracy of a gas partial pressures. Such a gas sensor includes a solid electrolyte and inert electrodes. The solid electrolyte, contained in the sensor, is selected in such a way that when an electrical current or voltage is applied, ions contained in the electrolyte form a reaction product with the gas to be determined in a secondary equilibrium reaction and with generation of an electrically measurable signal. Preferred solid electrolytes are $Na^+$-$\beta''$ aluminum oxide, NASICON, cubic stabilized zirconium oxide and polycrystals of tetragonal zirconium oxide. A method for the selective determination of gases using such electrodes also is described. Preferably an electrical current or voltage source shall be used which feeds a periodic, especially a sawtooth or sinusoidal signal, to the solid electrolyte, as a result of which the formed reaction product is decomposed to the same extent it was previously built up.

6 Claims, 10 Drawing Sheets

 Na-β"-ALUMINA
 Na$_2$CO$_3$
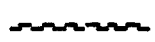 Pt FILM
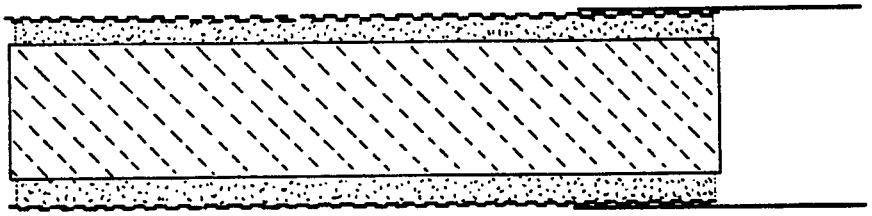
Fig. 2(a)
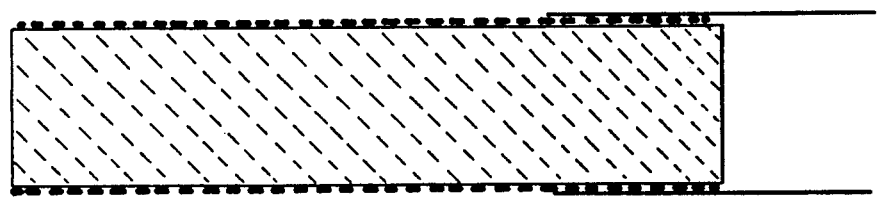
Fig. 2(b)
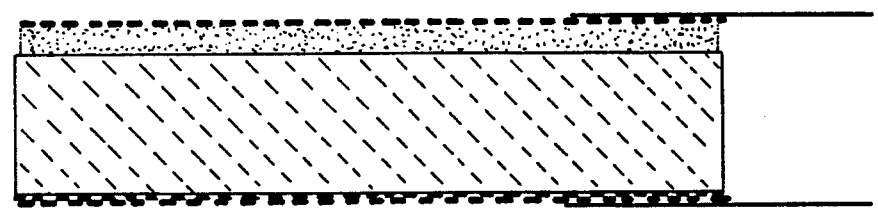
Fig. 2(c)

5,322,601

AMPEROMETRIC GAS SENSOR TO SELECTIVELY DETERMINE THE PARTIAL PRESSURES OF A GAS

FIELD OF THE INVENTION

The invention concerns an amperometric gas sensor to selectively determine with high accuracy the partial pressure of a gas and further it concerns a method using such a sensor.

BACKGROUND OF THE INVENTION

Analysis of gas mixtures and determination of the partial pressures of individual gases is gaining increasing significance. Accordingly gas sensors for automatic control in process sequences, for ecological monitoring and in biotechnology already are known. As a rule gas sensors make use of solid ionic conductors which offer many advantages compared to liquid electrolytes. A distinction is made regarding the sensors known to date between the potentiometric and the amperometric ones, the latter sometimes also being called polarographic sensors.

The earliest known gas sensors are potentiometric concentration cells with a gas electrode. The emf in them is according to Nernst's equation, $$E = \frac{RT}{nF} \ln\left(\frac{pO_2}{pO_{2(ref)}}\right)$$

where R is the gas constant, F the Faraday constant, T the absolute temperature and n the number of electrons taking part in the electrode reaction.

The first such cell that was used as a gas sensor contains zirconium oxide as the solid electrolyte and is composed as follows Pt, $O_2[pO_2(ref)]/ZrO_2(CaO)/O_2[pO_2]$, Pt.

If the partial pressure of the reference oxygen, i.e. its activity is kept constant in this early system, then the unknown partial pressure $pO_2$ can be measured by means of the voltage E.

Such zirconium-oxide electrolyte based oxygen sensors have been commercially available since about 1965. Moreover gas sensors also are now known which allow determining other gases such as $Cl_2$ and $SO_2/SO_3$ by means of solid electrolytes [J. Fouletier, Sensors and Actuators, 3, 1982-3, 295; and W. L. Worrell et al, Sensors and Actuators, 2, 1982, 385].

Potentiometric gas sensors already are known, in which the solid electrolyte evinces a modified surface layer. Such sensors are a voltaic cell composed as follows:

Reference-electrode/solid-electrolyte/modified surface-layer/electrical-conductor/gas.

In these sensors, the equilibrium between electrolyte and gas is set by additional intermediate layers, the so-called gas-sensitive layers. Conventionally a film or a thin layer together with the electrically conducting material is deposited on the electrolyte (German patent document A 2,926,172). A series of sensors based on this principle already is known, allowing to determine $Cl_2$, $NO_2$, $O_2$ and $CO_2$ (W. Weppner et al, Solid State Ionics, 18+19, 1986, 1223 and Weppner et al, Sensors and Actuators, 12, 1987, 449 and J. Liu and W. Weppner, Solid State Communications 76, 1990, 311).

Contrary to the above described potentiometric sensors, amperometric solid-electrolyte gas sensors are based on the principle of the saturation current. Amperometric sensors are significantly more sensitive to comparatively slight changes in pressure and therefore reveal the partial gas pressure with higher accuracy. Because the signal, namely the saturation current $I_{lim}$ is directly proportional to the partial gas pressure of the gas being measured, the measuring apparatus is much simplified. Moreover, the saturation current is comparatively insensitive to the system temperature and total pressure. Again amperometric sensors may be operated at substantially lower temperatures, that is at temperatures less by 200° C. than potentiometric sensors.

Amperometric sensors merely require a voltage high enough to drive the sensor in the region of the saturation current. Lastly, and contrary to the case for potentiometric gas sensors, amperometric gas sensors also can be operated without reference electrodes, as a result of which both design and operation are much simplified.

Such amperometric oxygen sensors already are known from Dietz in solid State, Ionics 6, 1982, 175 and from H. Jahnke et al, *Ber. Bunsenges. Phys. Chem.* 92, 1988, 1250 and from Takeuchi et al, *Chemical Sensor Technology* vol. 1, T Seuyama ed., Elsevia, Amsterdam, 1988, p 79. Cubic stabilized zirconium oxide (CSZ) is used in the sensors described therein.

SUMMARY OF THE INVENTION

Sensors operating on the principle of the saturation current suffer from the drawback that the gas must pass through the electrolyte. Accordingly it is the object of the invention to create a gas sensor overcoming the above drawbacks while retaining the advantages of the amperometric sensors.

This object is achieved by an amperometric gas sensor and a method for the selective determination of partial pressures of a gas with high accuracy. The said sensor consists of a solid electrolyte and inert electrodes. In the invention the solid electrolyte is selected in such a manner that it contains ions and/or an ion-forming compound which upon the application of a current or voltage to the electrolyte boundary surfaces forms a redox product with the gas in a reversible redox reaction in a secondary equilibrium. On account of the formation of the redox product, an electric charge in the form of chemical substances is bound, so that an electrically measurable signal is generated.

The invention also concerns a method for the selective amperometric determination of the pressures of one or more gasses next to each other in a solid electrolyte. The method is characterized in that an electrical current or voltage is applied to a solid electrolyte fitted with inert electrodes and in that a reversible redox product is induced at the electrolyte phase boundaries from at least one ion contained in the solid electrolyte and the gas in a secondary equilibrium reaction with dissipation or release of an electrical charge at the boundary surfaces, and in that the generated electrical signal is measured.

DESCRIPTION OF THE DRAWINGS

FIG. 2(a)-2(c) shows the set up of a cell of the invention;

DESCRIPTION OF THE PREFERRED EMBODIMENTS

Figure 1:
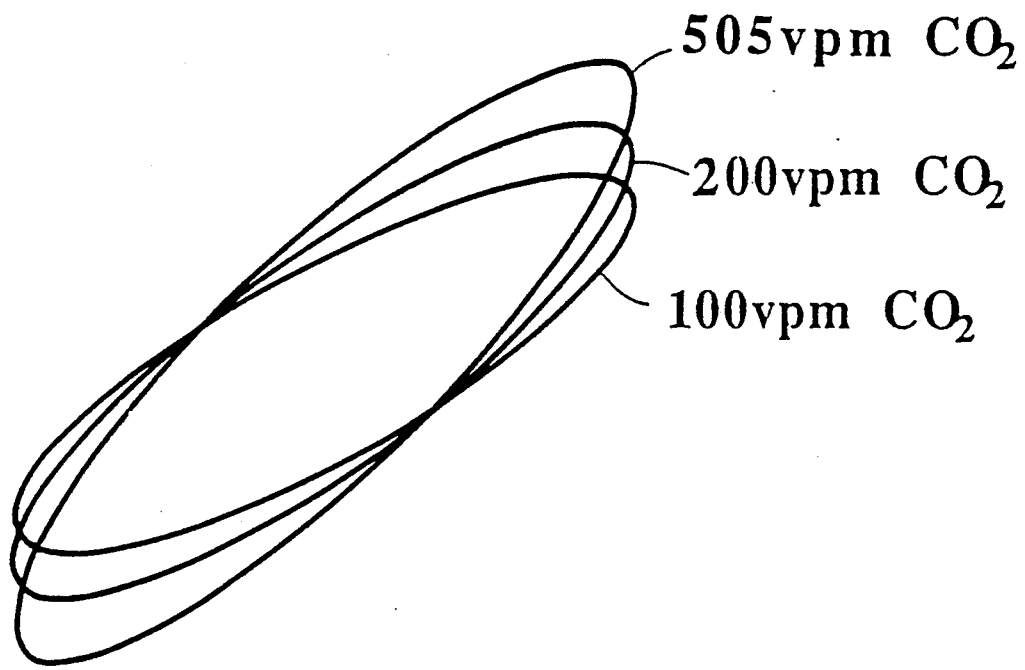
FIG. 1 shows the relationship between current and partial gas pressure.

The sensor consists of a solid electrolyte and inert electrodes. In the invention, the solid electrolyte is selected in such a manner that it contains ions and/or an ion-forming compound which upon the application of a current or voltage to the electrolyte boundary surfaces forms a redox product with the gas in a reversible redox reaction in a secondary equilibrium. Because of the formation of the redox product, an electric charge in the form of chemical substances is bound, so that an electrically measurable signal is generated.

In a preferred embodiment mode, the gas sensor of the invention comprises a thin sensor layer between the solid electrolyte and the inert electrode. The said layer consists of the reaction product of the electric-current induced product of the redox reaction of the secondary equilibrium, or the layer at least contains such a product in part, possibly together with other substances. In an especially preferred embodiment, such a sensor layer is mounted between the solid electrolyte and both inert electrodes.

The invention also concerns a method for the selective amperometric determination of the partial pressures of one or more gases next to each other in a solid electrolyte. The method is characterized in that an electrical current or voltage is applied to a solid electrolyte fitted with inert electrodes and in that a reversible redox product is induced at the electrolyte phase boundaries from at least one ion contained in the solid electrolyte and the gas in a secondary equilibrium reaction with dissipation or release of an electrical charge at the boundary surfaces, and in that the generated electrical signal is measured. In a preferred implementation of the invention, a periodic current or voltage is applied. This feature offers the advantage that the redox product from the reaction between the solid-electrolyte ions and the gas is permanently returned into its initial substances by the reversible reaction, so that these initial substances will not be consumed. The formation reaction then can be induced again with a new current or voltage pulse and the generated electrical signal again can be measured anew without the need of newly introducing the participating reagents required for the redox reaction into the phase boundary surface. Therefore the method of invention does not require substantial ion migration.

The kinetic control of the redox reaction makes it possible to determine the partial pressures of several gases when the redox products are formed at different rates. This can be achieved by a corresponding selection of the participating reagents. Such selection is known to the expert and is feasible by simple trials or without conceptual difficulties.

The inert electrodes to be used in the sensor of the invention are known to the expert. As a rule these are electrodes made of an electrically conducting material inert relative to the gas(es) to be measured. Preferred electrode materials are precious metals, especially platinum.

Again the solid electrolyte to be used in the method of the invention is known to the expert. In particular those solid electrolytes shall be used which contain ions that enter a reversible chemical redox reaction induced by current or voltage with the gas to be ascertained. Preferred solid electrolytes of the invention are $Na^+$-$\beta''$-aluminum oxide, NASICON, cubic stabilized zirconium oxide (CSZ) and polycrystals of tetragonal zirconium oxide (TZP) containing reactive ions. Preferred reactive ions are $Na^+$ and $Ca^{2+}$. Preferred periodic currents or voltages of the invention are sawtooth or sinusoidal waveshapes.

Again solid electrolytes are preferred from an intercalation compound of the general formula $A_xMX_2$, where A is selected from the group comprising Li, Na, K and H, M is a transition metal and preferably is from the group comprising Ti, V, Cr, Mn, Fe, Co, Ni, Y, Nb, Mo, Lh, Th, W, Re, and x is a value between 0 and the saturation range of the intercalation compound with A; preferably x is a figure between 0.5 and 1.2.

Especially preferred compounds are $Na_xCoO_2$ and $Na_xNiO_2$ and in particular the sodium compound $Na_{0.7}CoO_2$.

The kinetic or amperometric signal obtained by means of the gas sensor of the invention is linearly proportional to the gas concentration which must be ascertained and on account of the linear relation between signal and gas pressure, there is high sensitivity and a short response time. The principle of the gas sensor of the invention is that a slight electrical perturbation signal acts on the secondary chemical equilibrium forming at the phase boundary surfaces of the solid electrolyte between the electrolyte components and the gas to be determined, and that thereby this equilibrium is shifted reversibly.

The electrical perturbation signal may be a voltage or a current. Preferably a periodic perturbation signal shall be used that prevents continuous growth of the reaction product induced by the current or voltage and decomposes this reaction product to the same extent it was built up. The current generated in response to the perturbation signal is measured in the process. This current depends on the concentration of the gases taking part in the electrode reaction. The electrode reactions being different for different gases, the gas sensors of the invention therefore allow determining next to each other several different gases because of the different kinetic reaction constants.

The expert may easily select by trial the amplitude and frequency in such a manner that optimal sensitivity shall be achieved. These parameters depend on the particular electrode reactions and illustratively for $CO_2$ gas shall be 10 to 100 mv for a frequency of 0.5 Hz.

When a perturbation signal acts on the gas-sensitive electrodes of the ion conductor, the current as a rule will be composed of two parts, namely a Faraday component and a non-Faraday component. The non-Faraday component arises from charging and discharging the capacitor formed by the double layer of the boundary phase. The Faraday current arises from the reactions at the electrodes, that is, it depends on the concentration of the reagents and on the stoichiometric change of the gas-sensitive layer.

The redox reaction taking place at the electrode surface of the $Na^+$-$\beta''$-aluminum oxide electrolyte when determining $CO_2$ can be represented as follows:

$$O_2(gas) \rightleftharpoons O_2(ads) \rightleftharpoons 2O(ads)$$

$$CO_2(gas) \rightleftharpoons CO_2(ads)$$

$$Na^+(\beta''\text{-}Al_2O_3) \rightleftharpoons Na^+(Na_2CO_3)$$

$$O_2(ads) + 4e^- \rightleftharpoons 2O^{2-}(ads) \rightleftharpoons 2O^-(ads) + 2e^-$$

$$CO_2(ads) + O^{2-}(ads) \rightleftharpoons CO_3{}^{2-}(ads)$$

$$2Na^+ + CO_3{}^{2-} \rightleftharpoons Na_2CO_3.$$

If the cell of the invention is strongly polarized by the applied voltage, then the anode reaction can be described as follows:

$$Na_2CO_3 \rightarrow 2Na^+ + CO_2 + \tfrac{1}{2}O_2 + 2e^-.$$

In that case the following reaction takes place at the cathode:

$$2Na^+ + CO_2 + \tfrac{1}{2}O_2 + 2e^- \rightarrow Na_2CO_3.$$

Once equilibrium is achieved, in particular when applying a periodic voltage, the anode current $I_a$ and the cathode current $I_c$ will be equal.

The invention is elucidated below in relation to the drawings.

FIG. 1 shows the characteristic relationship between current and partial gas pressure. However, alternatively, the current may be controlled and the particular voltage required to maintain the current may be plotted.

FIG. 2(a) shows the set-up of a cell of the invention containing a solid electrolyte made of $Na^+$-$\beta''$ aluminum oxide ($\beta''$ type, Ceramatec, Salt Lake City, USA) a 300 Å thick $Na_2CO_3$ film together with a porous Pt film (200 Å) having been evaporated onto the electrolyte. FIGS. 2b and 2c show a symmetrical Pt/$Na^+$-$\beta''$-aluminum oxide/Pt cell and an asymmetric Pt/$Na^+$-$\beta''$-aluminum oxide/$Na_2CO_3$/Pt cell.

The cell of FIG. 2a was placed into a quartz tube crossed by a gas mixture of $CO_2$, $O_2$ and Ar at a rate of 200 cm³/min. The gas mixtures were controlled using a mass-flowmeter controller (F. C. Tylan, 280 and 260) and the temperature was controlled within ±1° C. by a Euroterm proportional temperature controller using a chromel-alumel thermocouple.

Figure 3:
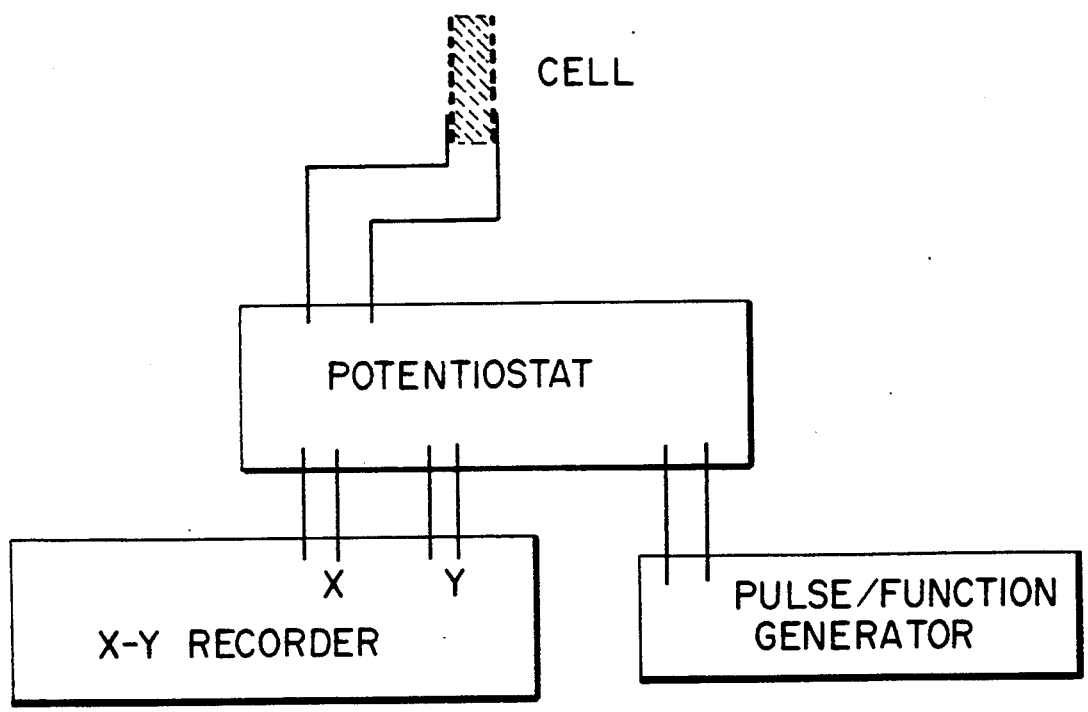
FIG. 3 shows the circuit for measurement.

FIG. 3 shows the electrical circuit for all measurements. A voltage was applied by a potentiostat (Jaissle IMP 83) to a voltaic cell of the invention. Then a sinusoidal or sawtooth voltage was generated using a Hewlett Packard generator 8116A and the reaction current was plotted as a function of the applied voltage. Following aging and equilibration of the cell of the invention in the system to be determined, a drive potential of low amplitude (10 to 100 mv) was applied at a frequency of 40 mHz.

Figure 4:
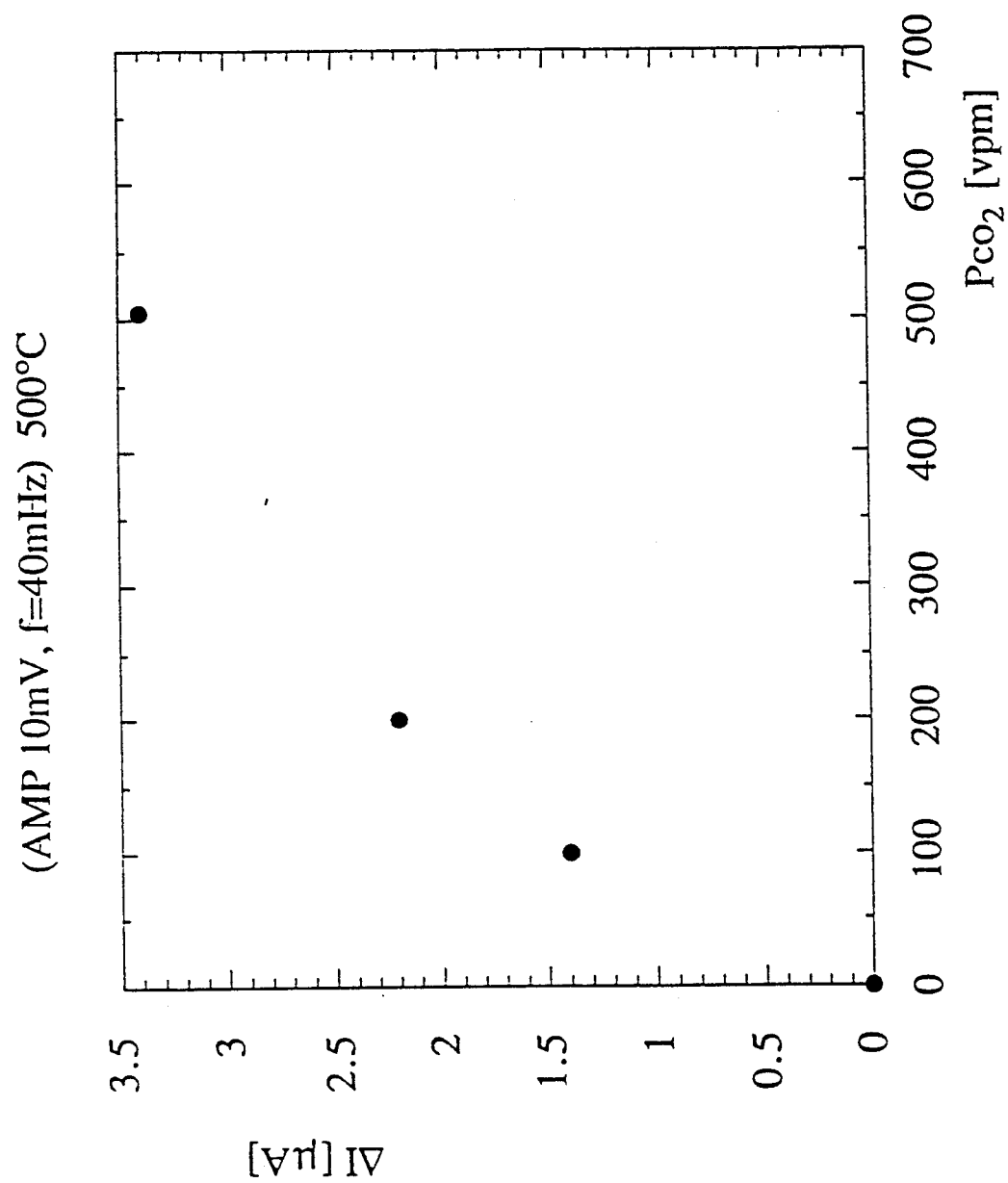
FIG. 4 shows the results for various $O_2$ concentrations.

FIG. 4 shows the results using the above set-up for various $O_2$ concentrations at 500° C. The maximum current magnitude increases with increasing $CO_2$ pressure. The resulting change in current $I^o$ is derived by subtracting the background current caused by a mixture of $O_2$-Ar free of $CO_2$.

Figure 5:
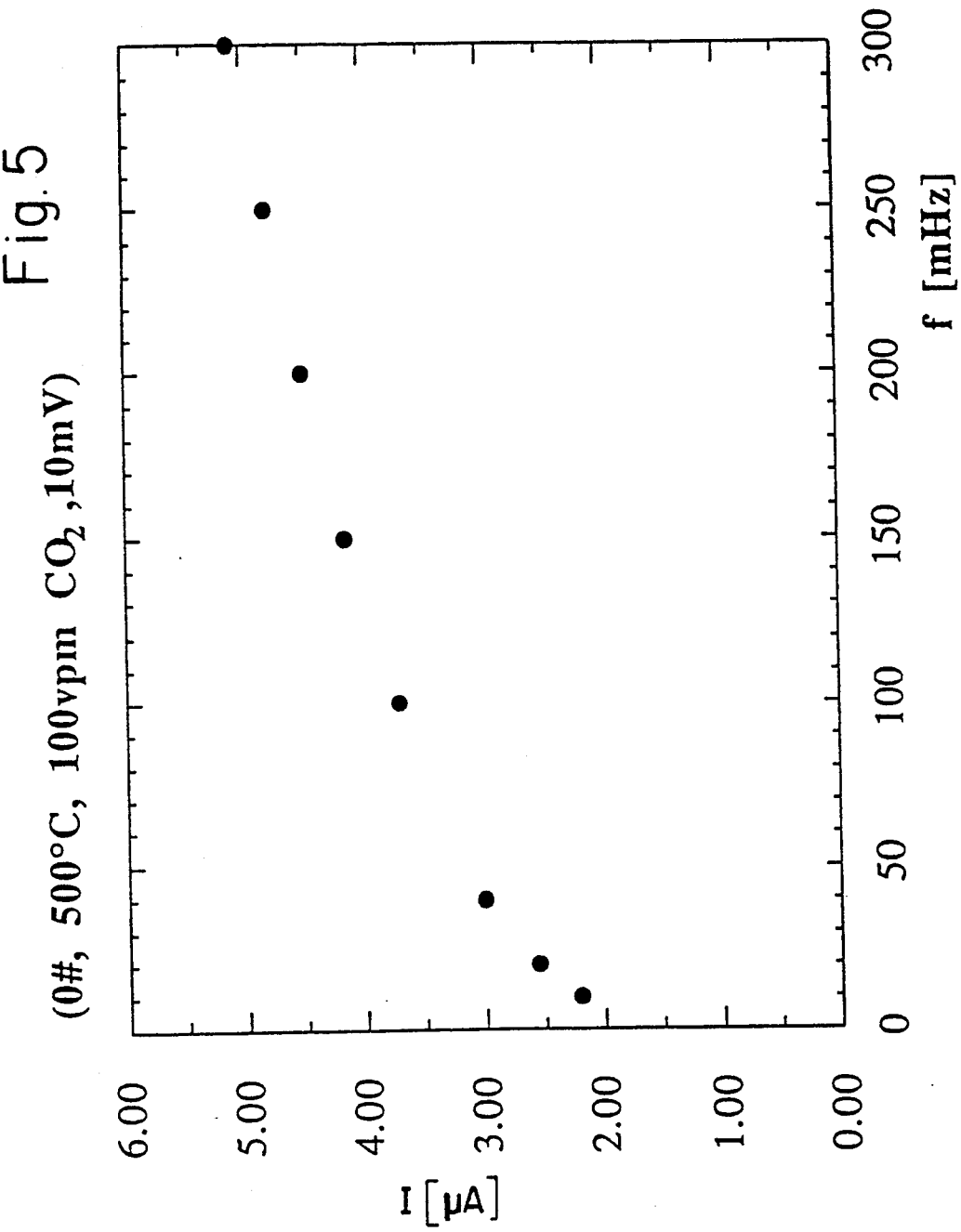
FIG. 5 shows the dependency on the drive-signal frequency for $CO_2$.

FIG. 5 shows the dependency on the drive-signal frequency for $CO_2$. It can be seen that as the frequency increases, the current also increases. The proportion of the non-Faraday current being proportional to the frequency, this frequency dependency can be used to determine the capacitance of the cell's double layer.

Figure 6:
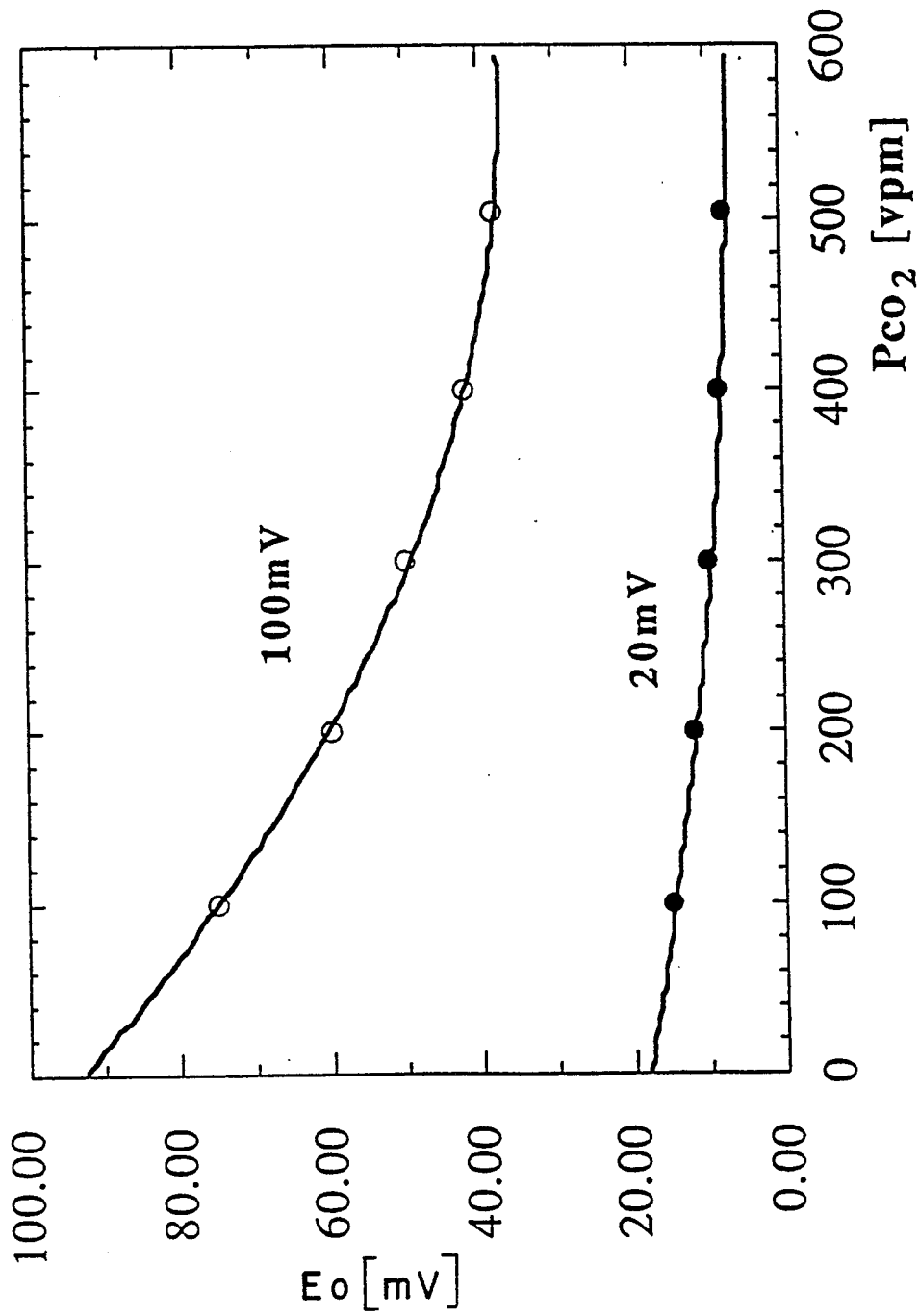
FIGS. 6 and 7 show the dependency of E0 and I0.
Figure 7:
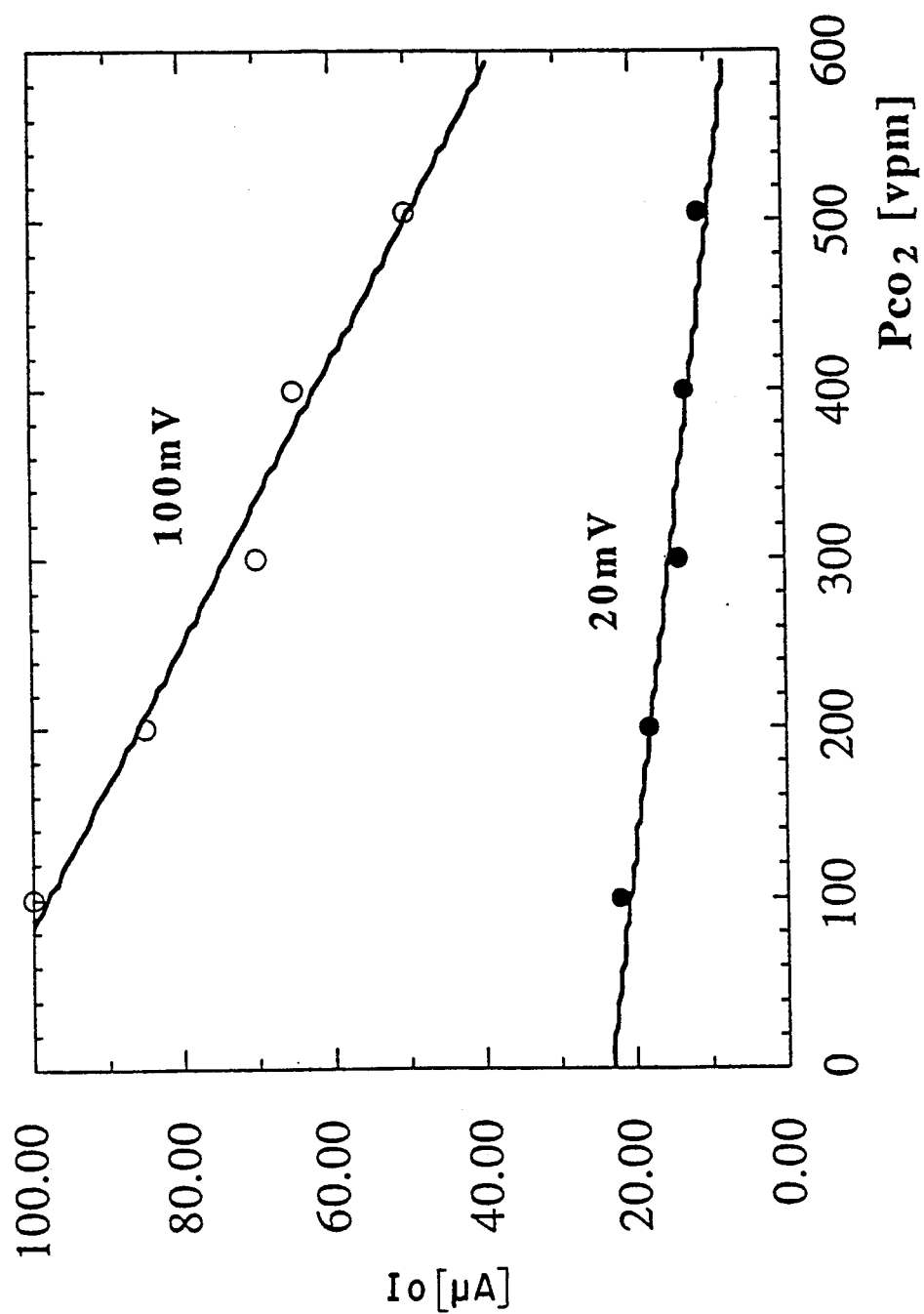

FIGS. 6, 7 show the dependency of E0 (namely the potential for current 0) and of I0 (the current when the voltage is 0). It is seen that E0 is larger at low partial pressures. This proves that the low reagent concentration causes large electrode polarization.

Figure 8:
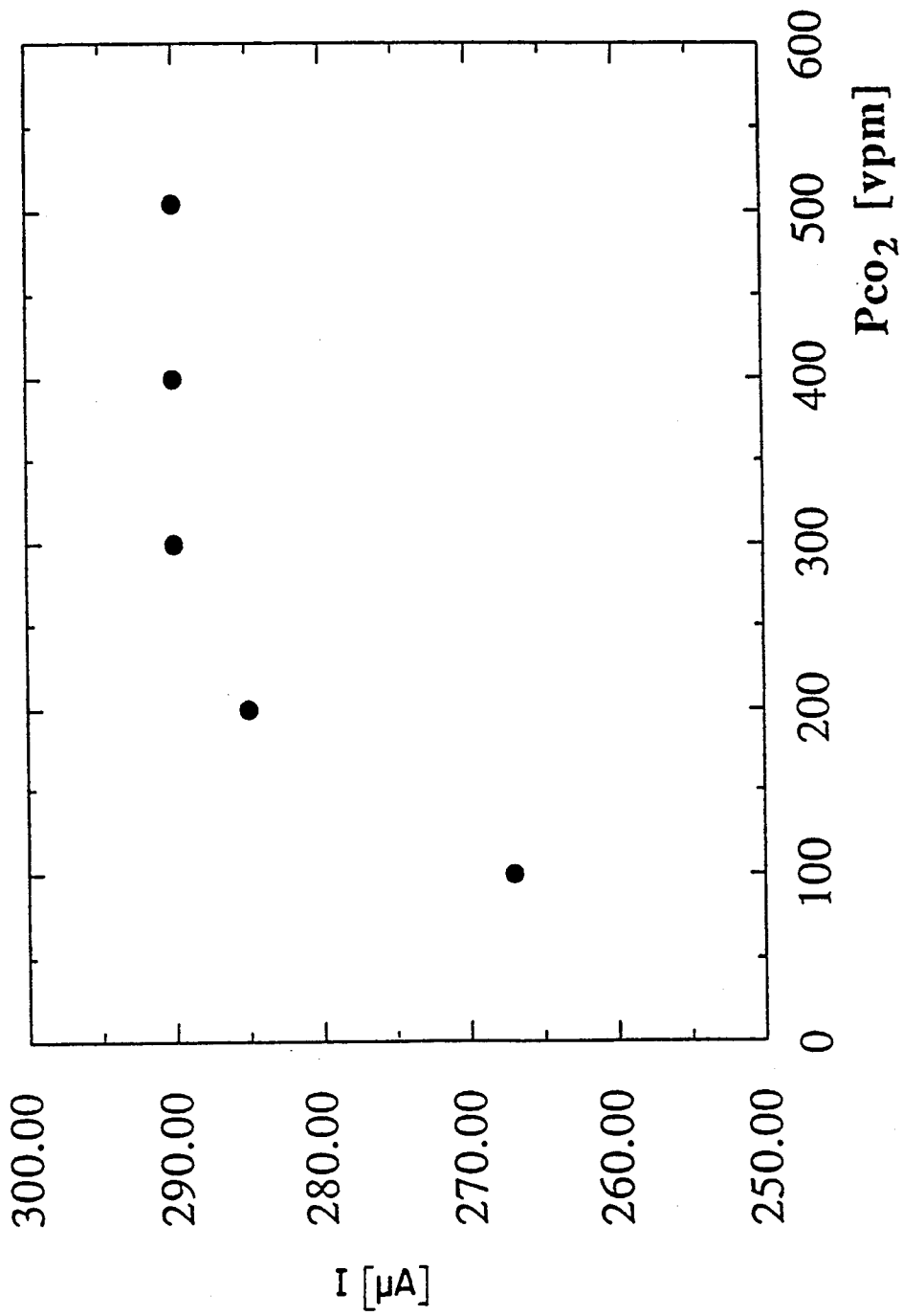
FIG. 8 shows the effect of the saturation current.

FIG. 8 shows the effect of the saturation current. It was found that for a $CO_2$ partial pressure > 300 vpm, the current amplitudes does not rise. This phenomenon arises because the slow sodium ion transport over the boundary surface or layers limits the electrode reactions, the $Na_2CO_3$ layer furthermore acting as a diffusion barrier.

Figure 9:
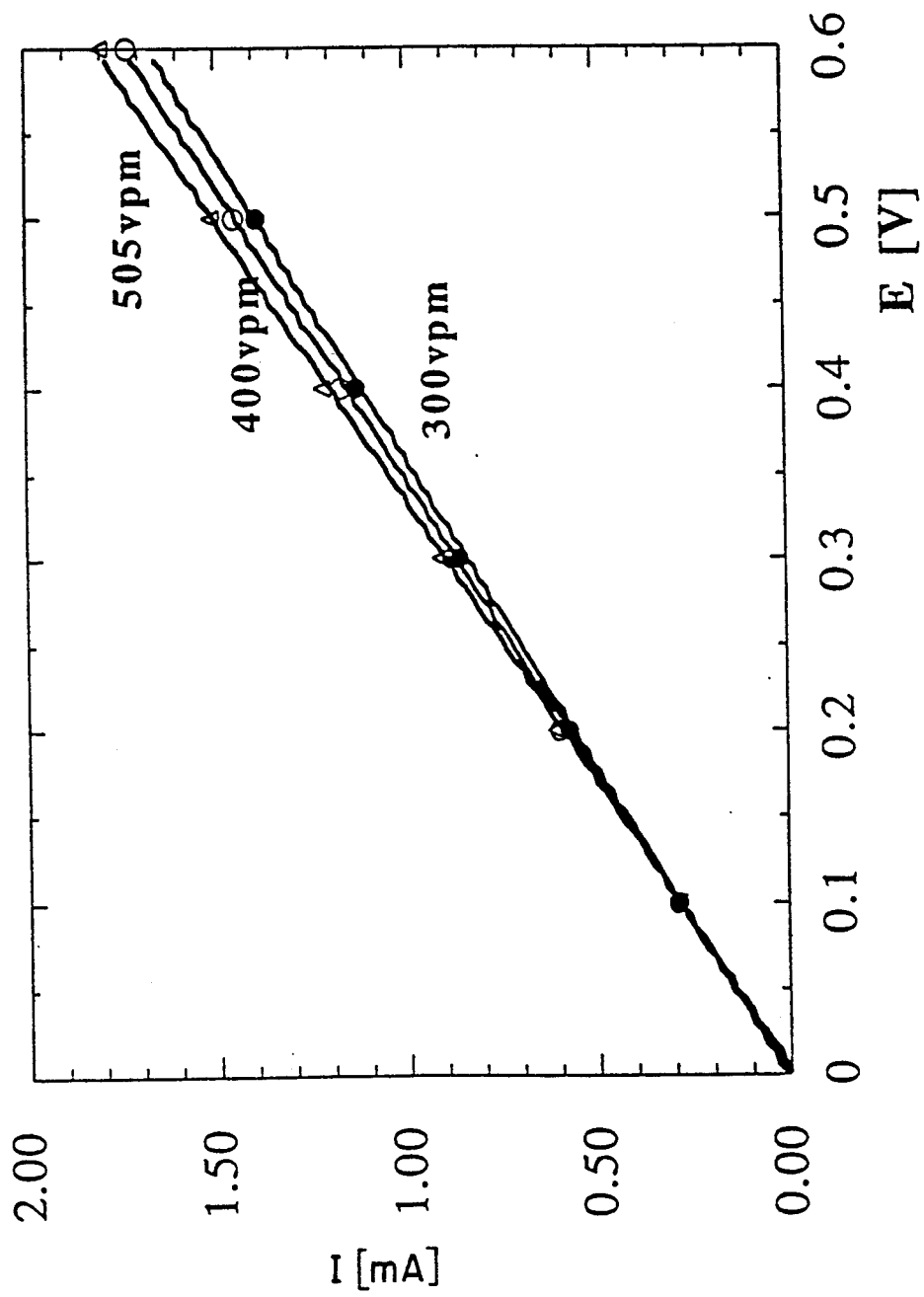
FIG. 9 shows the proportionality between current and voltage at constant $CO_2$ pressure.

FIG. 9 shows the proportionality between current and voltage at constant $CO_2$ pressure. This linear relation makes it plain that the impedance (i.e. the ratio of voltage-amplitude to current-amplitude) is larger than the resistance in the electrolyte. It follows that the boundary-layer process, which includes the charge transfer to the electrode surface, is the main contributor to the impedance.

Figure 10:
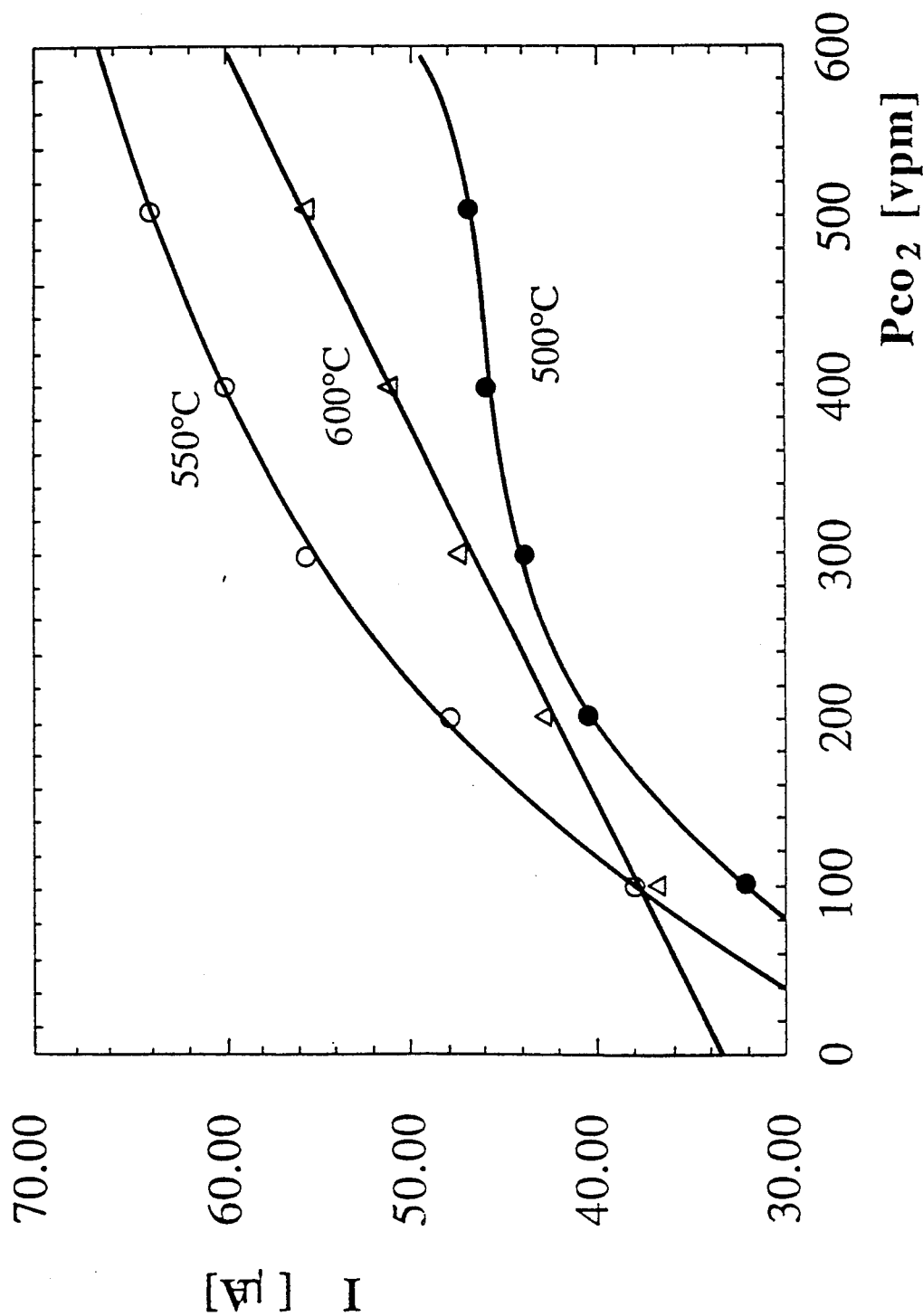
FIG. 10 shows the temperature-dependence of current-pressure curve.

FIG. 10 shows the temperature-dependence of current-pressure curve. As seen, the current-pressure relation becomes increasingly linear at higher temperatures, as a result of which slight changes in partial pressure can be measured especially accurately.

It was discovered in the invention that a voltaic cell can be made from a solid electrolyte with two symmetric or asymmetric electrodes, a change in current caused by a drive voltage lending itself to the determination of gas partial pressures. Such a voltaic cell of the invention is used as a gas sensor operated without a reference electrode. By suitably designing different sensor layers, the same voltaic cell can be used to determine different gases such as $NO_x$, $SO_2$, $CO_2$ and $O_2$.

What is claimed is:

1. A method for amperometrically selectively determining partial pressure of a gas or several gases next to each other comprising the steps of:
    applying an electrical current or voltage to a solid electrolyte fitted with inert electrodes;
    inducing a reversible redox product at phase boundary surfaces of said solid electrolyte from at least one ion, or a compound forming ions, contained in said solid electrolyte and the gas; and
    measuring an electrical signal so generated.

2. Method defined in claim 1, wherein a periodic current or voltage is used.

3. Method defined in either of claims 1 and 2, wherein said solid electrolyte contains alkali ions.

4. Method defined in claim 3, wherein said alkali ions are sodium ions.

5. Method defined in one of claims 1 or 2, wherein said solid electrolyte used is $Na^+$-$\beta''$-aluminum oxide or NASICON.

6. Method defined in one of claims 1 or 2, wherein the induced redox product is $Na_2CO_3$ and/or $Na_2O$.

* * * * *